United States Patent
Slater

(10) Patent No.: US 6,623,448 B2
(45) Date of Patent: Sep. 23, 2003

(54) STEERABLE DRUG DELIVERY DEVICE

(75) Inventor: Renee C. Slater, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/822,081

(22) Filed: Mar. 30, 2001

(65) Prior Publication Data

US 2002/0143291 A1 Oct. 3, 2002

(51) Int. Cl.[7] .................. A61M 31/00; A61M 37/00
(52) U.S. Cl. ................ 604/95.01; 604/104; 604/105
(58) Field of Search .............. 604/95.02, 104, 604/105, 106, 107, 280, 281, 95.01; 606/198

(56) References Cited

U.S. PATENT DOCUMENTS

| | | | |
|---|---|---|---|
| 4,723,936 A | | 2/1988 | Buchbinder et al. .......... 604/95 |
| 4,757,827 A | | 7/1988 | Buchbinder et al. ........ 128/772 |
| 4,998,916 A | | 3/1991 | Hammerslag et al. ........ 604/95 |
| 5,372,587 A | | 12/1994 | Hammerslag et al. ........ 604/95 |
| 5,885,258 A | * | 3/1999 | Sachdeva et al. ........... 600/141 |
| 6,004,269 A | * | 12/1999 | Crowley et al. ............. 600/374 |
| 6,078,831 A | * | 6/2000 | Belef et al. .................. 600/424 |
| 6,102,890 A | | 8/2000 | Stivland et al. ............... 604/96 |
| 6,183,444 B1 | * | 2/2001 | Glines et al. ................ 604/187 |
| 6,248,112 B1 | * | 6/2001 | Gambale et al. ............ 606/108 |
| 6,346,099 B1 | * | 2/2002 | Altman ................... 604/164.01 |

\* cited by examiner

*Primary Examiner*—Robin O. Evans
(74) *Attorney, Agent, or Firm*—Squire, Sanders & Dempsey, L.L.P.

(57) ABSTRACT

A medical apparatus used to deliver a therapeutic substance. The medical apparatus provides a catheter assembly, which includes a translating body assembly and a fixed body assembly mated together in a telescopic configuration to allow the translating body assembly to move relative to the fixed body assembly and facilitate the delivery of the therapeutic substance to a targeted area. The catheter assembly also provides a steering assembly capable of moving the distal portion of the catheter assembly between a first direction and a second direction. A guiding catheter including an anchoring device can be used to secure the catheter assembly in position at the targeted area to facilitate deployment of a needle for delivering the therapeutic substance to the targeted area.

33 Claims, 12 Drawing Sheets

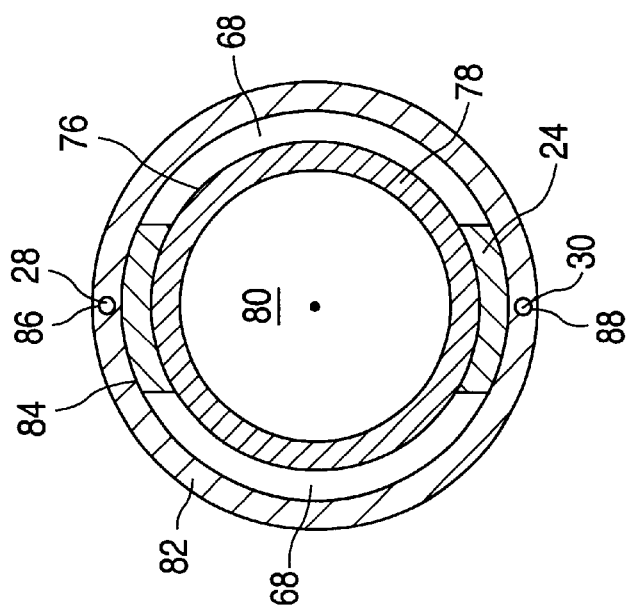
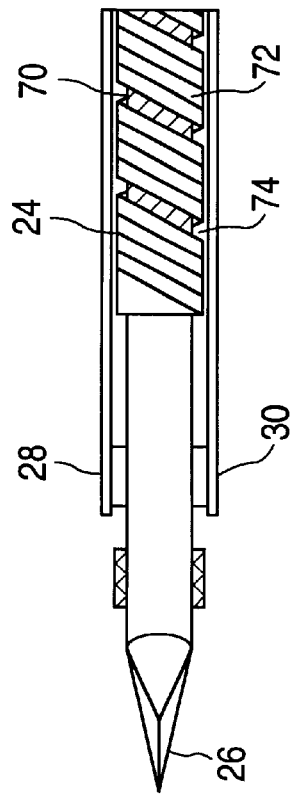
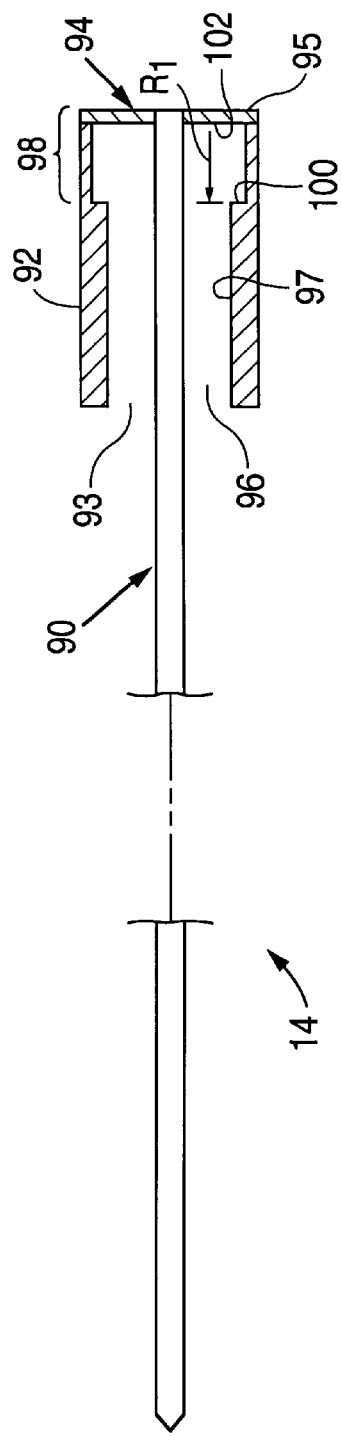
FIG. 7
FIG. 6
FIG. 8

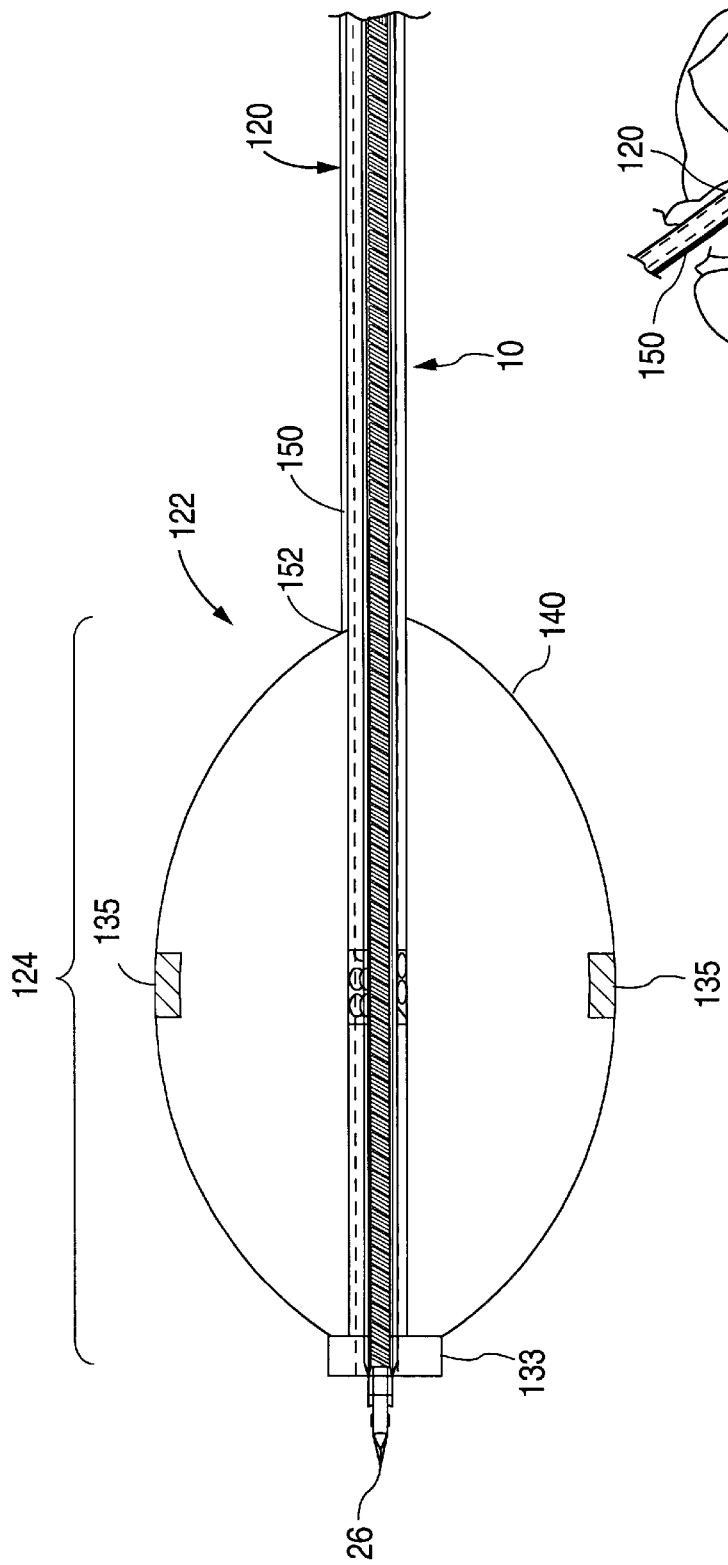
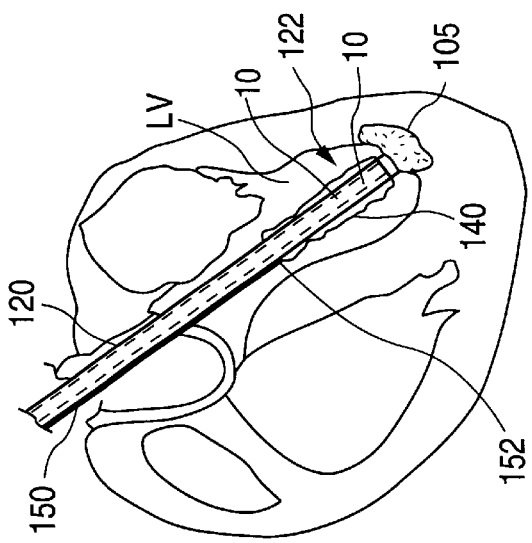
FIG. 12A
FIG. 12B

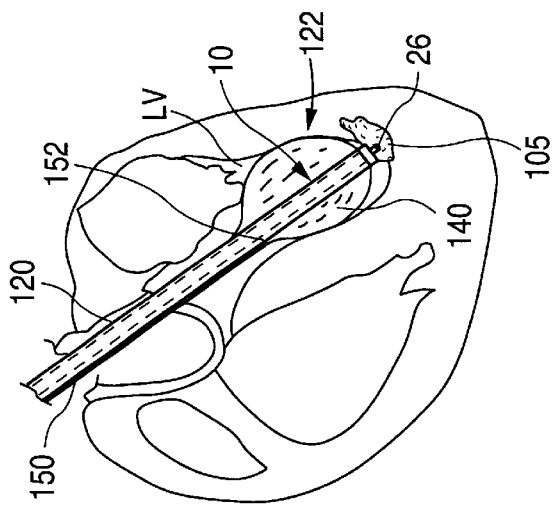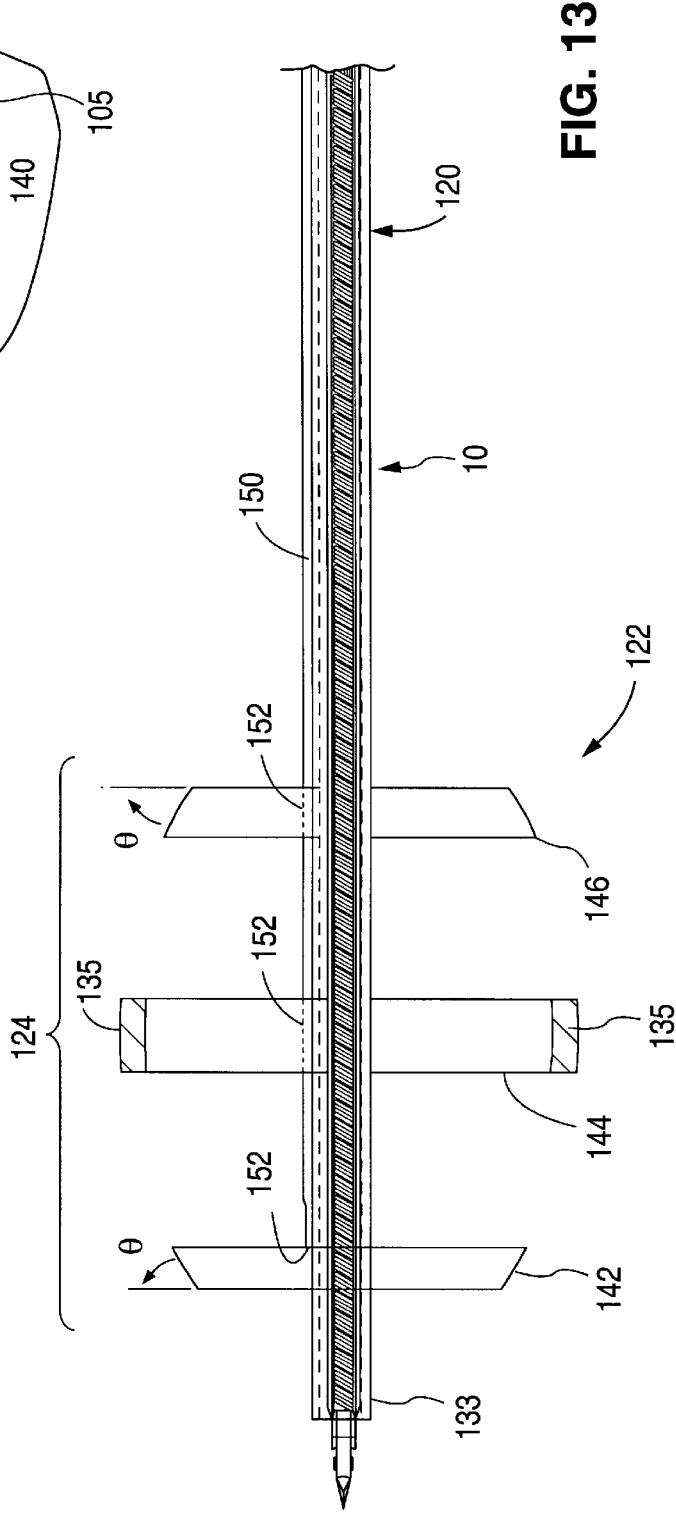
FIG. 12C
FIG. 13

STEERABLE DRUG DELIVERY DEVICE

BACKGROUND

1. Field of the Invention

The present invention relates to an apparatus for locating and positioning a medical device in a patient. More particularly, the present invention relates to a medical device for delivering therapeutic substances, which is steerable through body lumen or cavities and positionable within organs or tissue from a position external to the body.

2. Related Art

The number and variety of medical devices available to repair the effects of cardiovascular disease has increased rapidly over the last several years. More particularly, alternatives to open heart surgery and cardiovascular by-pass surgery have been extensively investigated, resulting in the development of non-surgical procedures. These procedures are typically directed toward the reduction of stenosis within the vasculature of a patient or the generation of new blood vessels in the body for restoring blood flow to tissues after injury or trauma.

Some medical devices, such as those developed to control the effects and occurrence of angiogenesis, such as Percutaneous TransMyocardial Revascularization (PTMR) and gene therapy, may use a catheter for delivering therapeutic substances to diseased vessels and ischemic myocardium. Angiogenesis is a naturally occurring process, both in health and in disease states, where new blood vessels are grown in the body for healing wounds and for restoring blood flow to tissues after injury or trauma. For example, in females, angiogenesis occurs during the monthly reproductive cycle to rebuild the uterus lining and to mature the egg during ovulation. Angiogenesis also occurs in various disease states, such as cancer, diabetic blindness, age-related macular degeneration, rheumatoid arthritis, coronary artery disease, stroke, and other disorders.

Although angiogenesis occurs naturally in the body, various procedures have been developed to artificially control the occurrence and effects of angiogenesis. For example in a PTMR procedure, a laser is used to create small channels in the diseased tissue. The channels re-establish direct blood flow to the tissue and allow oxygen-rich blood to saturate the oxygen-starved tissue.

Another procedure used to promote angiogenesis involves gene therapy. For this procedure, genetic material is delivered directly to the diseased area of the body. In particular, genetic material, such as Vascular Endothelial Growth Factor (VEGF), is incorporated into gene delivery vehicles called vectors, which encapsulate therapeutic genes for delivery to the diseased cells. Many of the vectors currently in use are based on attenuated or modified versions of viruses. The vectors may also be synthetic versions in which complexes of DNA, proteins, or lipids are formed into particles capable of efficiently transferring genetic material.

Medical devices used for non-surgical procedures, such as PTMR and gene therapy, generally include elongate tube-like members (e.g., catheters), which may be inserted into the body, either percutaneously or via a body orifice. Such medical applications frequently require the use of catheters having the ability to negotiate a variety of tortuous body lumens and body cavities. Many attempts have been made to provide catheters that are steerable to enable the catheter to be aimed at specifically targeted tissue or advanced through tortuous body lumens and/or body cavities. For example, in one type of balloon catheter a deflection wire is provided which extends along the entire length of the catheter. One drawback associated with this type of balloon catheter is that the deflection wire can be axially displaced to cause deflection of the catheter tip in only one direction. Thus, to be guided, the entire catheter must be rotated or torqued. Moreover, the design can require a relatively large diameter deflection wire, which can substantially increase the diameter of the catheter so as to preclude the use of the catheter in small lumen coronary applications. Limited catheter tip steerability results in greater time spent in the body and significantly elevated risk of trauma both to the vascular intima and to the patient in general.

SUMMARY

The present invention provides a medical apparatus and method of use for delivering a therapeutic substance to a target location in the human vasculature, for example, to control the effects and occurrence of angiogenesis. The present invention provides a catheter assembly that can be steered through the vasculature in more than one direction, without the need for rotating or torqueing the catheter assembly. Increased steerability can result in less time spent in the body and significantly reduce the risk of trauma both to the vascular intima and to the patient in general.

The invention provides a catheter assembly, which can be used for delivering the therapeutic substance to diseased vessels and ischemic myocardium. The catheter assembly can include a translating body assembly and a fixed body assembly mated together in a telescopic configuration to allow the translating body assembly to move relative to the fixed body assembly and facilitate the delivery of the therapeutic substance to a targeted area. The translating body assembly includes an inner member, which can be modified to provide flexibility, pushability (i.e., column strength) and torqueability to the inner member. The modification can be made substantially on the distal section of the inner member to allow the inner member to be steered to contact diseased tissue and to navigate through tortuous coronary lumen. The modified distal section provides enough flexibility to facilitate the steering of the distal tip, while maintaining enough column strength to provide adequate pushability and torqueability. A hollow needle can be coupled to the distal end of the modified inner member to penetrate through tissue and enable delivery of therapeutic substances to the tissue.

To provide steerability to the modified inner member, the translating body assembly can also include a steering device, which can include two tendons coupled along the sides and fixed distally to the inner member proximal to the hollow needle. The design of the catheter assembly maintains a relatively small diameter, since the dual-tendon arrangement minimizes the need for a large diameter deflection wire. Each tendon is coupled to a puller at the proximal section of the catheter assembly. Movement of the puller causes each tendon to move the distal section of the inner member. Beneficially, the catheter assembly can be displaced in at least two directions to cause deflection of the catheter assembly.

In one aspect of the invention, a guiding catheter including an anchoring device is provided in accordance with the present invention. The guiding catheter can be a hollow sheath having an inner lumen that extends the length of the sheath. The inner lumen is sized to slidably receive various intraventricular devices, such as the catheter assembly. The anchoring device is disposed at the distal end of the guiding catheter to aid in guiding the catheter assembly to the treatment area and for holding the catheter assembly in position to facilitate the extension of the hollow needle into the target tissue. Once in the treatment area, the anchoring device can be actuated and secured using friction and compressive forces. The distal end of the catheter assembly can be delivered through the lumen, such that the needle can be oriented at the designated treatment area using the pullers. The operator holds the handhold and urges the translating body assembly forward, which causes the hollow needle to move out from the distal end of the outer member and engage the tissue. Once the needle is engaged with the tissue, therapeutic substances can be delivered to the tissue.

These and other features and advantages of the present invention will be more readily apparent from the detailed description of the embodiments, set forth below, taken in conjunction with the accompanying drawings.

BRIEF DESCRIPTION OF THE DRAWINGS

FIG. 6 is a simplified sectional view of another embodiment of the inner member;

FIG. 7 is a simplified cross-sectional view of an embodiment of an inner member;

FIG. 8 is a simplified sectional view of the fixed body assembly of the catheter assembly of FIG. 1;

FIGS. 12A–12C are simplified illustrations of another embodiment of an anchoring device in accordance with the present invention; and FIG. 13 is a simplified illustration of yet another embodiment of an anchoring device in accordance with the present invention.

The features of the described embodiments are specifically set forth in the appended claims. However, the embodiments are best understood by referring to the following description and accompanying drawings, in which similar parts are identified by like reference numerals.

DETAILED DESCRIPTION

Figure 1:
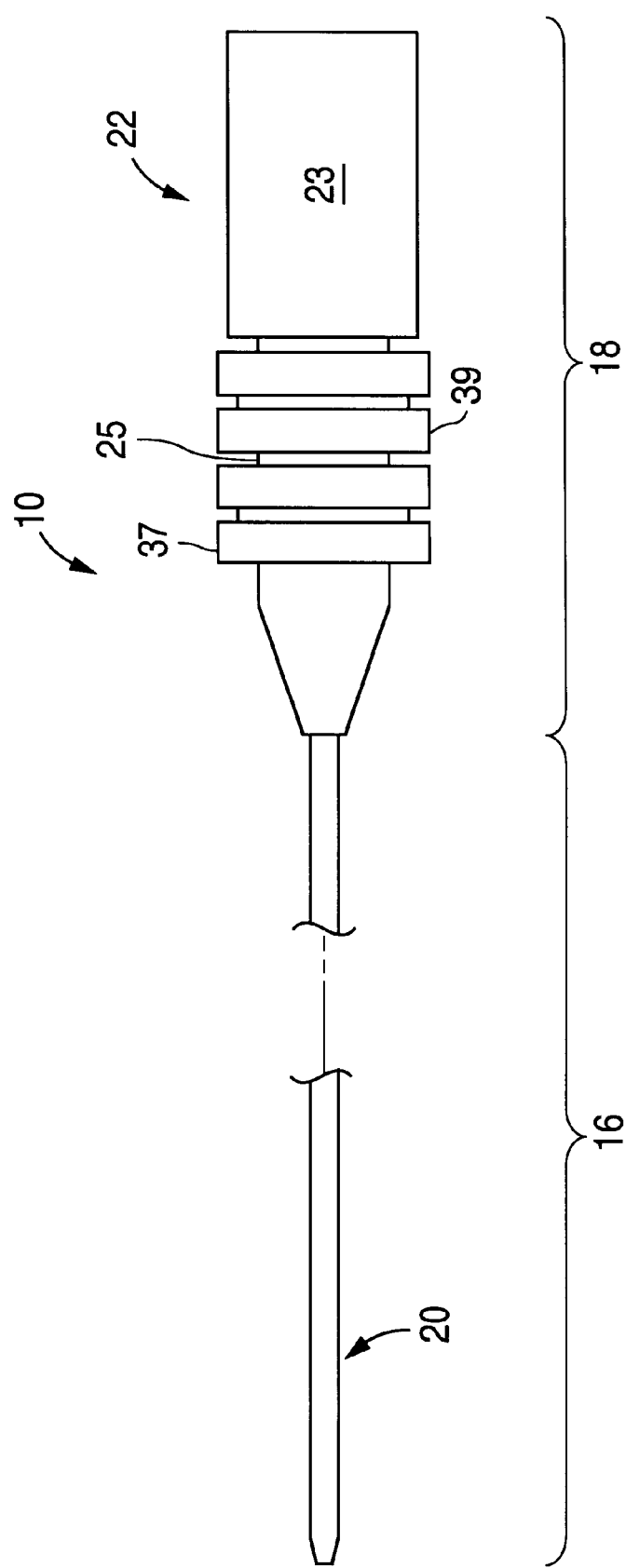
FIG. 1 illustrates an external view of the catheter assembly in accordance with one embodiment of the present invention.

Referring now to the drawings, wherein similar parts are identified by like reference numerals, a substance delivery catheter assembly is disclosed in accordance with one embodiment. In general, the substance delivery catheter assembly provides for delivering a substance, such as a therapeutic substance or a combination of therapeutic substances, to treat a localized area of a physiological lumen or the tissue of a body cavity or a body organ.

The term "therapeutic substance(s)," as used herein, refers to all drugs, compositions, genetic materials, growth factors, angiogenic substances, therapeutic agents, diagnostic agents/reagents and other similar chemical/biological agents, including combinations thereof, used to treat and/or diagnose restenosis, thrombosis, angiogenesis and related conditions.

FIG. 1 illustrates an external view of catheter assembly 10, which may be used to deliver a therapeutic substance, for example, to control the effects and occurrence of angiogenesis in diseased vessels and ischemic myocardium. Catheter assembly 10 can include an elongated, insertion portion 16 and a handle portion 18. Insertion portion 16 defines a distal end 20 and handle portion 18 defines a proximal end 22 of catheter assembly 10. As described in detail below, disposed within insertion portion 16 and handle portion 18 are components of translating body assembly 12 (FIG. 2) and fixed body assembly 14 (FIG. 8), which are configured to be assembled together in a telescopic arrangement to facilitate the delivery of the therapeutic substance to the targeted area.

Translating Body Assembly

Figure 2:
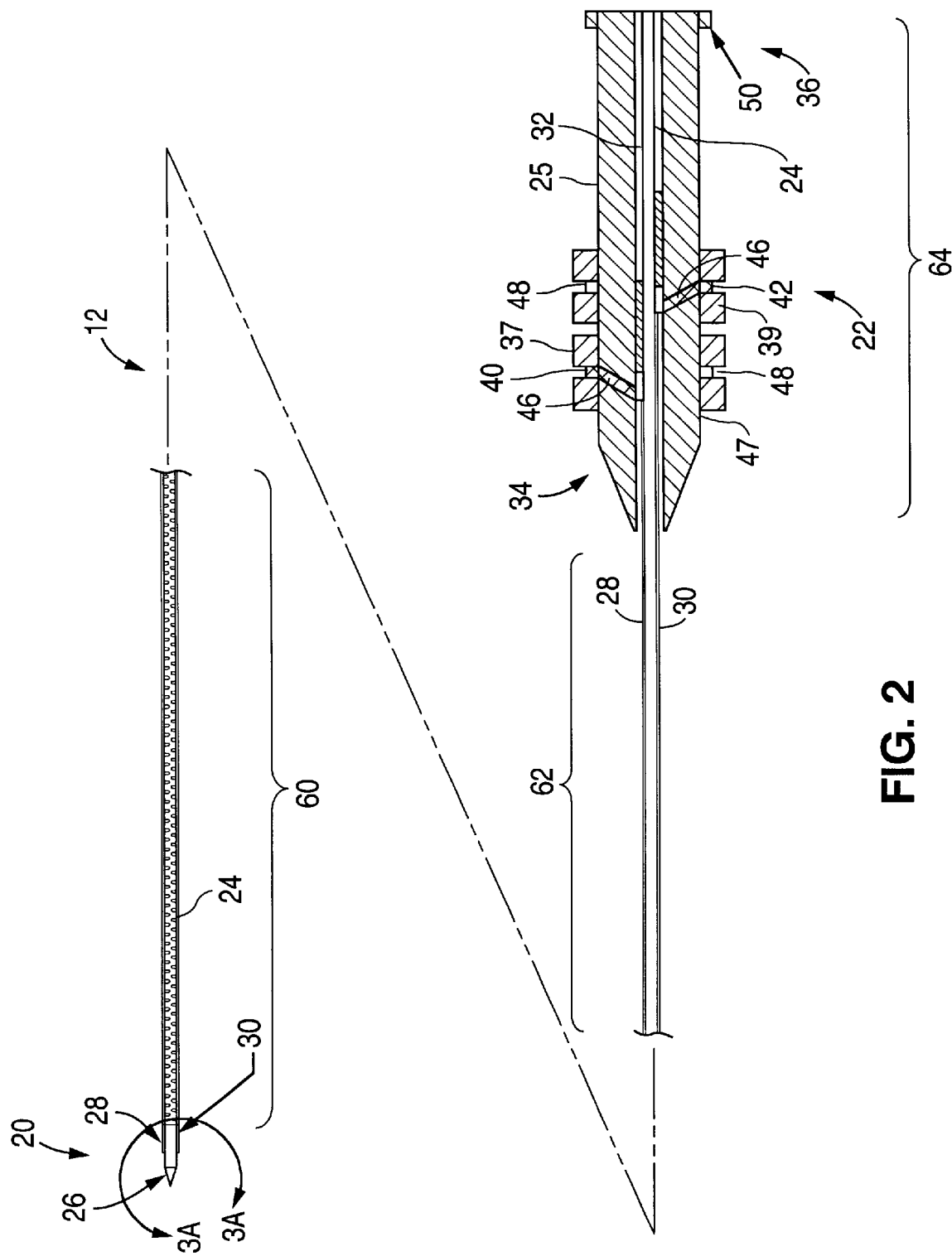
FIG. 2 is a simplified sectional view of the translating body assembly of the catheter assembly of FIG. 1.

FIG. 2 is a sectional view of translating body assembly 12 in accordance with one embodiment. Insertion portion 16 (FIG. 1) of translating body assembly 12 includes an inner member 24, a needle 26, and a steering device, which can include at least two steering tendons, for example, first steering tendon 28 and second steering tendon 30 coupled to opposing sides of the distal end of inner member 24. Inner member 24 and first and second steering tendons 28 and 30 extend the length of insertion portion 16 and into handle portion 18 (FIG. 1).

Handle portion 18 includes a translating member 25 having a distal end 34, a proximal end 36, and a hollow, bored-out inner portion 32 extending therebetween. Translating member 25 also includes pullers 37 and 39, which can be independently and rotatably coupled to an outer surface 47 of translating member 25 using a conventional technique, such as by using a roller bearing, detents, and the like. Slots 40 and 42 can be formed into translating member 25, which provide a conduit from inner portion 32 to outer surface 47 of translating member 25.

First steering tendon 28 and second steering tendon 30 enter into hollow portion 32 at the distal end 34 of translating member 25. Each steering tendon 28 and 30 can be threaded through slots 40 and 42 to be coupled to pullers 37 and 39. Movement of pullers 37 and 39 (e.g., rotation) causes first and second steering tendons 28 and 30 to pull on distal end 20 of inner member 24. For example, as first puller 37 is rotated clockwise, tension is applied to first steering tendon 28 causing distal section 20 of inner member 24 to be pulled in a first direction. As second puller 39 is rotated counterclockwise, tension is applied to second steering tendon 30, causing distal section 20 to move in a second direction. It should be understood that as tension is applied to one steering tendon, the other steering tendon is allowed to slack.

In one embodiment, a biasing device 46, such as a spring or similar device, can be coupled between an end of steering tendons 28 and 30 and pullers 37 and 39, respectively, to reside in slots 40 and 42. Biasing device 46 allows the non-tensioned tendon to lengthen when the other opposing tendon is being pulled. For example, when tension is applied to first steering tendon 28 to steer needle 26, second steering tendon 30 can lengthen to avoid binding second puller 39.

Optionally, pullers 37 and 39 can be formed with a groove 48 formed circumferentially around the body of pullers 37 and 39. In one embodiment, each slot 40 and 42 can terminate into one of grooves 48, such that steering tendons 28 and 30 can extend into grooves 48 where they are coupled to pullers 37 and 39. In this manner, as pullers 37 and 39 are rotated first and second steering tendons 28 and 30 can be wrapped/unwrapped around pullers 37 and 39 within grooves 48.

In one embodiment, a stopping member 50 can be positioned on proximal end 36 of translating member 25. As described in greater detail below, stopping member 50 controls the travel length of translating member 25 as it moves distally relative to fixed body assembly 14 (FIG. 8). In this embodiment, stopping member 50 can be a ring, a plate or any other member that, when coupled to proximal end 36 of translating member 25, extends out beyond the outside diameter of translating member 25. In this configuration, stopping member 50 can be made to contact a surface of fixed body assembly 14 to interfere with the movement of translating member 25.

Figure 3A:
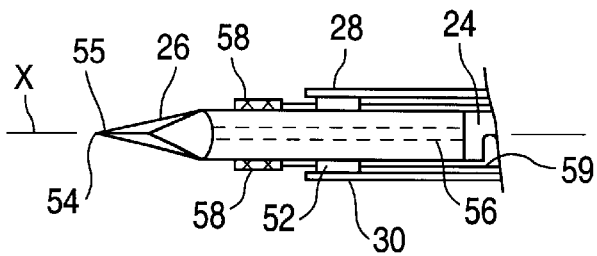
FIGS. 3A and 3B are simplified sectional views of the distal section of the translating body assembly of FIG. 2.

FIG. 3A shows a sectional view of a portion of the distal end of translating body assembly 12. The figure illustrates an embodiment, showing first steering tendon 28 and second steering tendon 30 coupled on opposing sides of inner member 24 using a conventional coupling technique 52, such as an adhesive or an epoxy or by welding, soldering, swaging and the like. FIG. 3A also illustrates needle 26 coupled to inner member 24 at the distal end of inner member 24. Needle 26 is coupled to inner member 24 using conventional techniques, such as adhesives, welding, soldering, swaging, and the like. Needle 26 includes a tissue-piercing tip 54 having a dispensing port 55. Dispensing port 55 is in fluid communication with a central lumen 56 of needle 26. Central lumen 56 of needle 26 extends through needle 26 to be in fluid communication with the inner lumen of inner member 24, which couples dispensing port 55 with a source of the therapeutic substance. Needle 26 is used to penetrate through tissue and enable delivery of therapeutic substances to the tissue.

Figure 3B:
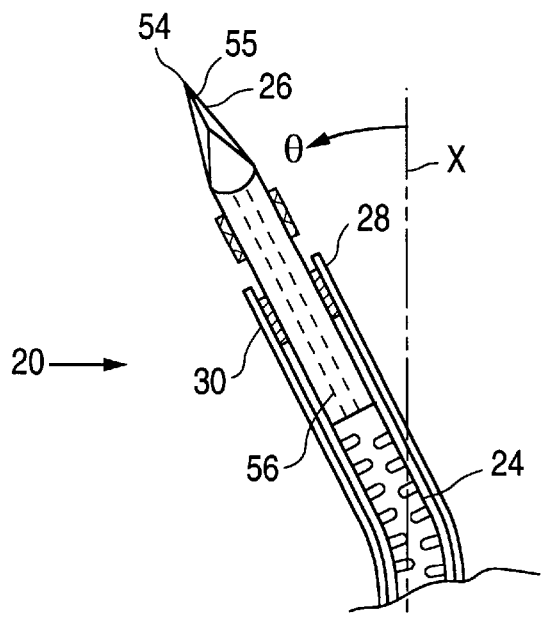

As shown in FIGS. 3A and 3B, distal end 20 of catheter assembly 10, which includes needle 26, can be moved from a first or deployment position, where needle 26 is axially aligned with axis x and a second or steered position, where needle 26 is moved off of axis x. In one embodiment, the off axis movement of needle 26 is caused by the steering tendons. For example, referring to FIG. 3B, a tension is applied to second steering tendon 30 caused by rotating second puller 39 (FIG. 2). Flexible inner member 24 bends as it is being pulled in the direction of the tensed steering tendon 30. First steering tendon. 28 is allowed to slack, or alternatively, biasing device 46 (FIG. 2) expands allowing steering tendon 28 to stretch. Needle 26 is returned to the axially aligned deployment position by releasing second puller 39 and removing the tension applied to steering tendon 30. In an alternative embodiment a third steering tendon or a fourth steering tendon can be similarly coupled to distal end 20 of catheter assembly 10 to further increase the extent of the steering capability. In one embodiment, needle 26 can be moved off of axis x an angle θ. Angle θ can range from about 0° to up to about 90°; preferably about 45°.

Referring again to FIG. 3A, a radiopaque marker 58, or alternatively a plurality of radiopaque markers 58, can be positioned proximal to needle 26 to indicate to the operator, the location of needle 26 while in the body. In general, radiopaque markers 58 may be made from a variety of suitable materials opaque to X-rays, such as platinum, gold, tungsten, tantalum and the like, to act as a marker to aid in precise positioning of needle 26. The use of radiopaque markers for this purpose is well known and understood by those of ordinary skill in the art.

Figure 4:
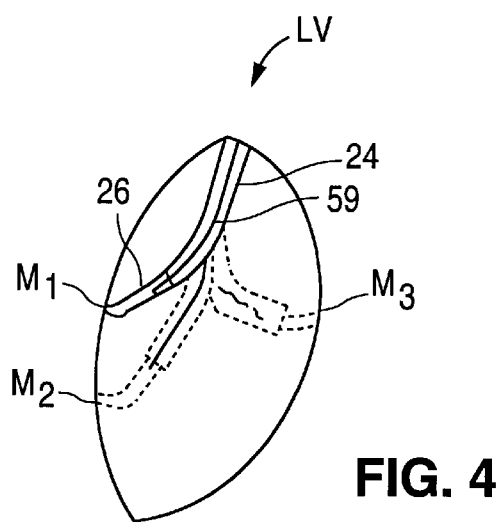
FIG. 4 is a simplified illustration of the catheter assembly being used to map the inner surface of the ventricle wall according to one embodiment.

In one embodiment, a lead wire 59 may be coupled to at least one radiopaque marker 58 to provide positioning feedback from needle 26. Lead wire 59 provides a path for electrical signals to be passed back and forth between markers 58 and a receiver (not shown). In this embodiment, the target treatment area, such as the left ventricle LV of the heart, can be mapped. As best understood with reference to FIG. 4, to obtain a longitudinal, or sectional view of the tissue of the left ventricle LV, inner member 24 can be slowly moved into the left ventricle LV where needle 26 is allowed to contact various points on the surfaces of the left ventricle, for example, points $m_1, m_2 \ldots m_n$. In this manner, needle 26 can be used as a transducer, which generates a signal upon contact with points $m_1, m_2 \ldots m_n$. The signal is then relayed via lead wire 59 to the receiver (e.g., an image processor). The data points are processed using well-known and understood image processing techniques. The image processor creates a representative illustration of a cross-section of the left ventricle LV. The single, sectional image of the left ventricle LV can be displayed on a monitor for the operator to view. Additional sectional images can be generated as the needle 26 (acting as a transducer) is slowly moved longitudinally through the left ventricle LV. The sectional images are collected and processed, or stacked, by the image processing system. The developing longitudinal view of the left ventricle LV can be displayed on a monitor as well. Therefore, a two-dimensional cross-sectional image of the left ventricle or a three-dimensional longitudinal view of the left ventricle is possible.

Figure 5A:
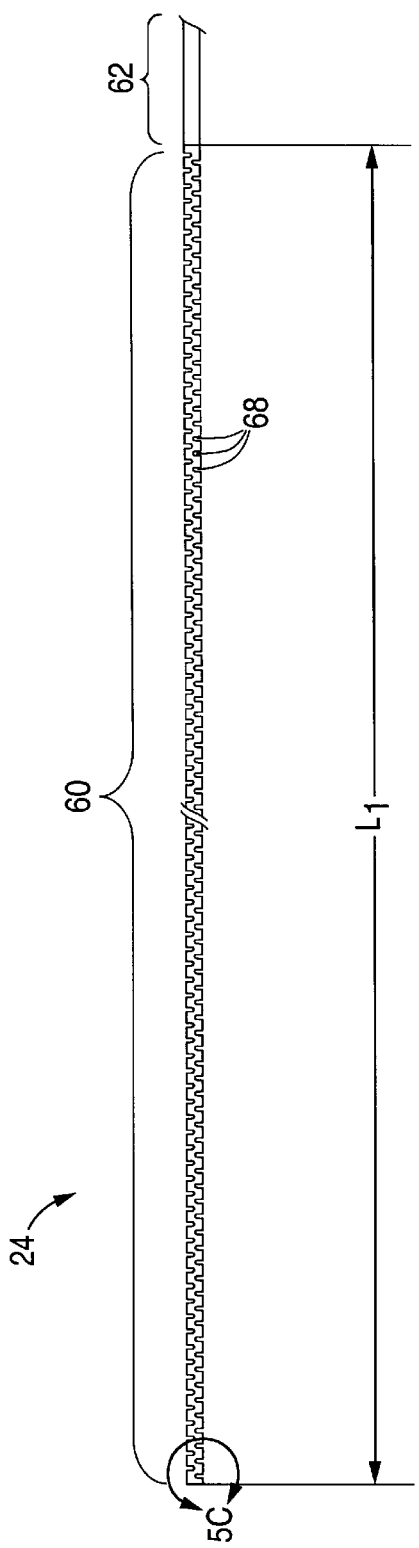
FIGS. 5A and 5B are simplified illustrations of an inner member in accordance with embodiments of the present invention.

FIG. 5A is a sectional view of inner member 24 in accordance with one embodiment. Inner member 24 of translating body assembly 12 may be any length from about 0.100 inches to over about 12 inches, depending upon the intended application. In one embodiment, inner member 24 can be between about 135 cm and about 180 cm in length; preferably about 180 cm, as is typical of many existing catheters. It should be understood that the actual length of inner member 24 is a function of the application.

Figure 5B:
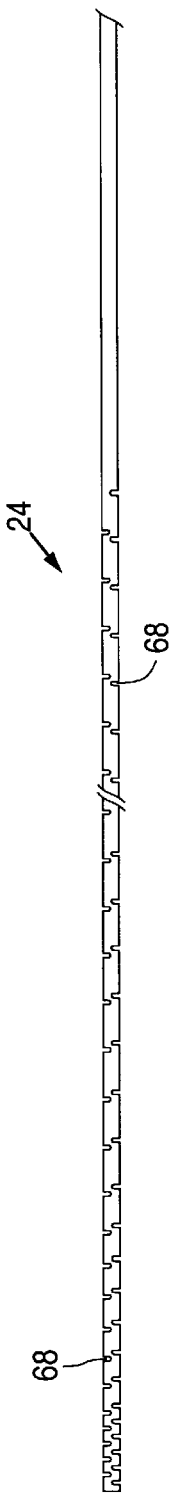
Figure 5C:
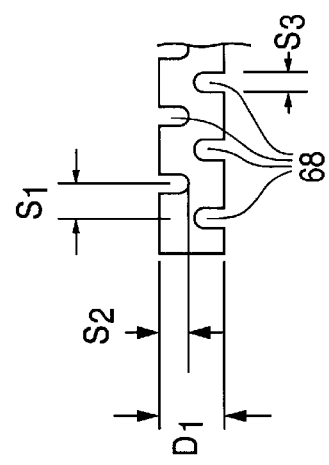
FIG. 5C is a simplified sectional view of the distal end of the inner member of FIG. 5A.

Inner member 24 can be constructed in any of a variety of ways. In one embodiment, inner member 24 is a tubular member formed of a hypotube. A hypotube, as the term is used herein, refers generally to a metallic tube having a lumen therethrough. In this embodiment, hypotube 24 can be a thin-walled, stainless steel tubing. The external diameter of hypotube 24 is a function of the intended application and can be varied to optimize and maintain a sufficiently small exterior diameter for the intended application. For example, as shown in FIG. 5C, hypotube 24 can have an external diameter $D_1$ in the range of from about 0.028 inches to about 0.0425 inches.

In one embodiment, hypotube 24 includes three regions, a modified region 60, an intermediate region 62 (FIG. 2) and a fixed region 64 (FIG. 2). Modified region 60 can be tailored to have increased flexibility, which allows distal end 20 to be steerable. Intermediate region 62 is a non-modified portion of inner member 24. Fixed region 64 is the portion of inner member 24 that is inserted and fixed into translating member 25 (FIG. 2).

Modified region 60, disposed just proximal to needle 26, is a flexible but controllable steerable region. Modified region 60 can be fabricated to facilitate lateral displacement of needle 26 relative to the central axis of inner member 24, through physical design and/or choice of flexible construction materials (FIG. 3B). As shown in FIGS. 5A and 5B, modified region 60 of hypotube 24 can be made to have increased flexibility, for example, by forming a pattern of indentations 68, such as notches, serrations, slots, openings, grooves, channels and the like, on the surface of hypotube 24. Indentations 68 can be arranged along a length $L_1$ of hypotube 24. Length $L_1$ can range from between about 4 inches and about 11 inches; preferably about 6 inches. Each indentation 68 can be spaced apart a suitable distance $S_1$. In one embodiment, $S_1$ can range from between about 0.006 inches and 0.015 inches. Indentations 68 can have a depth $S_2$ of between about 1% and 50% of the outer diameter $D_1$ of inner member 24. The width $S_3$ of indentations 68 can vary between about 0.004 inches and 0.010 inches; preferably 0.008 inches.

In an alternative embodiment shown in FIG. 5B, the pattern of indentations 68 can be varied so that the flexibility gradually decreases (i.e., gets stiffer) proximally along hypotube 24. In this alternative embodiment, spacing $S_1$ can be varied along length $L_1$ such that indentations 68 at the distal end of hypotube 24 are closer together than indentations 68 at the proximal end of length $L_1$.

FIG. 6 illustrates yet another embodiment of inner member 24. In this embodiment, modified region 60 of inner member 24 is created by winding a first coil layer 70 of metal wire in a first coiled direction and winding a second coil layer 72 of metal wire over first coil layer 70 in a second coiled direction. In this embodiment, the revolutions of wire per unit of axial distance along inner member 24 is reduced in second coil layer 72 relative to first coil layer 70 to provide a looser wound coil having space between coil loops. For example, first coil layer 70 can be tightly wound to provide column strength and pushability, while second coil layer 72 can be more loosely wound around first coil layer 70 with spaces 74 between each coil loop to provide flexibility. In another example, first coil layer 70 may be wound in a left-hand lay and second coil layer 72 may be wound in a right-hand lay, such that as a torque is applied to inner member 24 the first coil layer 70 expands while the second coil layer 72 contracts to increase the torqueability of inner member 24 while maintaining flexibility.

The amount of torqueability, pushability, and strength depend on the application and can be modified by varying the size, shape, and number of wires used in first coil layer 70 and second coil layer 72. In one embodiment, the metal wire can be a high tensile strength wire of a resilient, non-corrosive metal, such as stainless steel or platinum. The wire may be a flat wire having a rectangular cross-section with a width of between about 0.002 inches and 0.004 inches, and a length of between about 0.004 inches and 0.010 inches. The wire may alternatively have a cross-section of other variations known in the art. The cross-section and dimensions of the wire-wound inner member 24 can be a function of the intended application.

FIG. 7 is a cross-sectional view of one embodiment of inner member 24. In this embodiment, an elastic, biocompatible coating or sheath 78 can be applied to interior wall 76 of lumen 80 of inner member 24 to keep the therapeutic substance within lumen 80, such that none of the therapeutic substance is lost through slots 68. Alternatively, a coating or sheath 82 can be applied to exterior 84 of inner member 24 instead of, or in addition to, coating 78. In this alternative embodiment, coating 82 can include a pair of opposed steering tendon lumens 86 and 88 in which steering tendons 28 and 30 can be received. Dipping, spraying or wrapping and heat fusing techniques, as are known by those of ordinary skill in the art, can form suitable coatings. Alternatively, heat shrinkable tubing can provide a suitable sheath 82. The coating material is selected to be substantially chemically inert in the in vivo vascular environment, to permit sufficient flexing of inner member 24 without cracking, and to minimize sliding friction of inner member 24 within fixed assembly 14 (FIG. 8). A variety of materials are suitable for coatings 78 and 82, such as polytetrafluoroethylene, urethane or polyethylene.

Fixed Body Assembly

Figure 9:
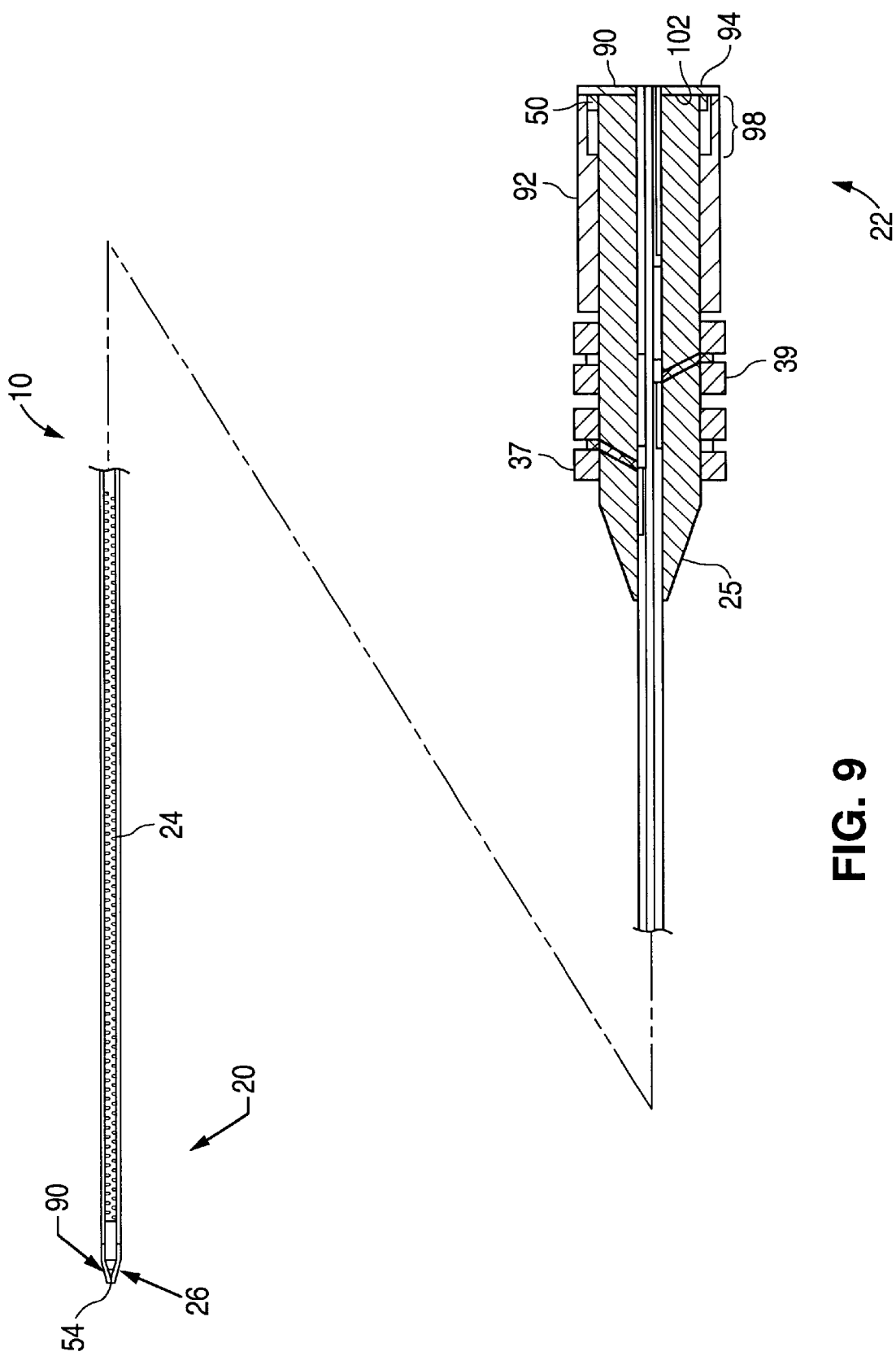
FIG. 9 is a sectional view of the assembled catheter assembly having a therapeutic substance needle in a retracted position.

FIG. 8 is a sectional view of fixed body assembly 14 in accordance with one embodiment. In this embodiment, fixed body assembly 14 includes an outer member 90, a proximal handhold 92 and an endplate 94. In one embodiment, outer member 90 can be a flexible sheath, made of a material, such as polytetrafluoroethylene, urethane, polyethylene and the like, having an inner lumen (not shown) extending therethrough. The sheath inner lumen is sized to slidably receive inner member 24, steering tendons 28 and 30 and needle 26 (FIG. 9). Handhold 92 is designed to be gripped by the human hand, and thus, can have any suitable external shape and size. For example, hand-hold 92 can have a cylindrically shaped body, which defines a cylindrical hollowed out inner portion or cavity 96 extending the length of hand-hold 92 and sized to slidably receive translating member 25 (FIG. 2). Handhold 92 also defines an open distal end 93 and a proximal open end 95. End plate 94 can be mounted using conventional techniques to handhold 92, such that end plate 94 encloses cavity 96 at open proximal end 95. A proximal end of outer member 90 can be inserted through open distal end 93 and into cavity 96 and secured to endplate 94. In this configuration, outer member 90 remains fixed to, and stationary with, handhold 92 during operation of catheter assembly 10.

In one embodiment, a counter-bore region 98 having a diameter larger than the diameter of cavity 96 can be formed, cut and/or machined into the inner wall 97 of cavity 96. Counter-bore region 98 can extend distally from open proximal end 95 a distance $R_1$, which may vary depending on the application. A shoulder 100 is formed by the junction between counter-bore region 98 and cavity 96 at distance $R_1$ from open proximal end 95.

Figure 10:
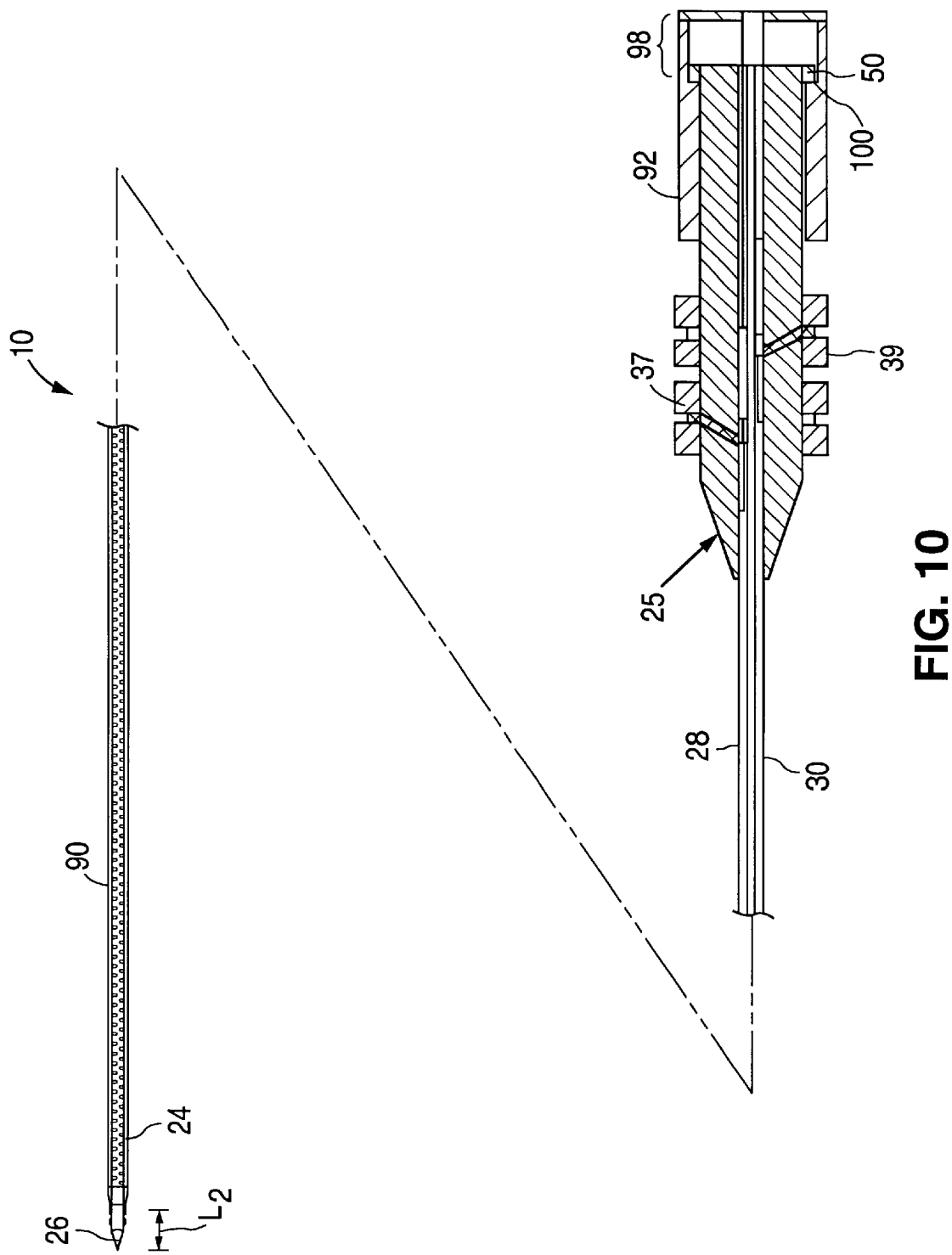
FIG. 10 is a sectional view of the assembled catheter assembly having a therapeutic substance needle in an extended position.

As shown in FIGS. 9 and 10, cavity 96 and counter-bore region 98 are formed to allow movement of translating body assembly 12 relative to fixed body assembly 14. Counter-bore region 98 also provides an area to secure translating member 25 to hand-hold 92 and to control the travel of translating member 25. Translating member 25 is slidably moveable within cavity 96 while stopping member 50, disposed on proximal end 36 of translating member 25, is confined to counter-bore region 98. Since the outer diameter of stopping member 50 is greater than the outer diameter of translating member 25 but lesser than the diameter of counter-bore region 98, the distal movement of translating member 25 relative to hand-hold 92 is limited distally by shoulder 100. The proximal movement of translating member 25 relative to handhold 92 is limited by surface 102 of endplate 94. Accordingly, distance $R_1$ represents the approximate range of movement in which translating member 25 can operate.

As best understood with reference to FIG. 9, translating member 25 can be moved distally and proximally relative to hand-hold 92 at least the length of travel $R_1$ provided in counter-bore region 98. When translating member 25 is moved to a furthest proximal position, stopping member 50 contacts surface 102 of endplate 94. In this configuration, at distal end 20 of catheter assembly 10, needle 26 is in its first or retracted position, where tissue-piercing tip 54 is located inboard of outer member 90, so as to avoid damaging tissue during deployment of catheter assembly 10.

As best understood with reference to FIG. 10, translating member 25 can be urged distally relative to hand-hold 92 until stopping member 50 contacts surface 100. At distal end 20 of catheter assembly 10, needle 26 is moved from the retracted first position to an extended second position. In its second or extended position, tissue-piercing tip 54 is located outboard of outer member 90, so as to permit needle tip 54 to penetrate the tissue of, for example, the ischemic myocardium. Needle 26 can be made to protrude from outer member 90 any predetermined length, the specific length being dependent upon the desired depth of calibrated penetration and the procedure for which catheter assembly 10 is to be used. The protruding length $L_2$ of needle 26 can be from about 1 mm to about 5 mm.

Anchoring Device

In some instances, as needle 26 is advanced to contact the tissue surface, the resistance of the tissue to needle penetration may have a tendency to cause catheter assembly 10 to "push back" in a direction approximately opposite to the direction of needle advancement/penetration. In this situation, an anchoring device can be deployed to securely position catheter assembly 10 and, thus, needle 26, within the target area and avoid the push back effect. Accordingly, needle 26 can be extended a predetermined depth into the tissue allowing accurate delivery therapeutic substances to the target area and, thus, enhance treatment capabilities.

Figure 11A:
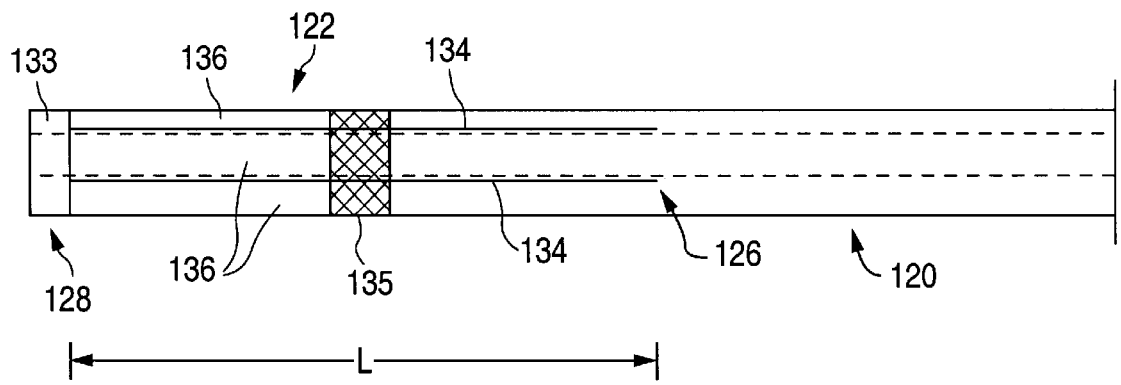
FIG. 11A is a simplified illustration of an embodiment of an anchoring device in accordance with the present invention.
Figure 11B:
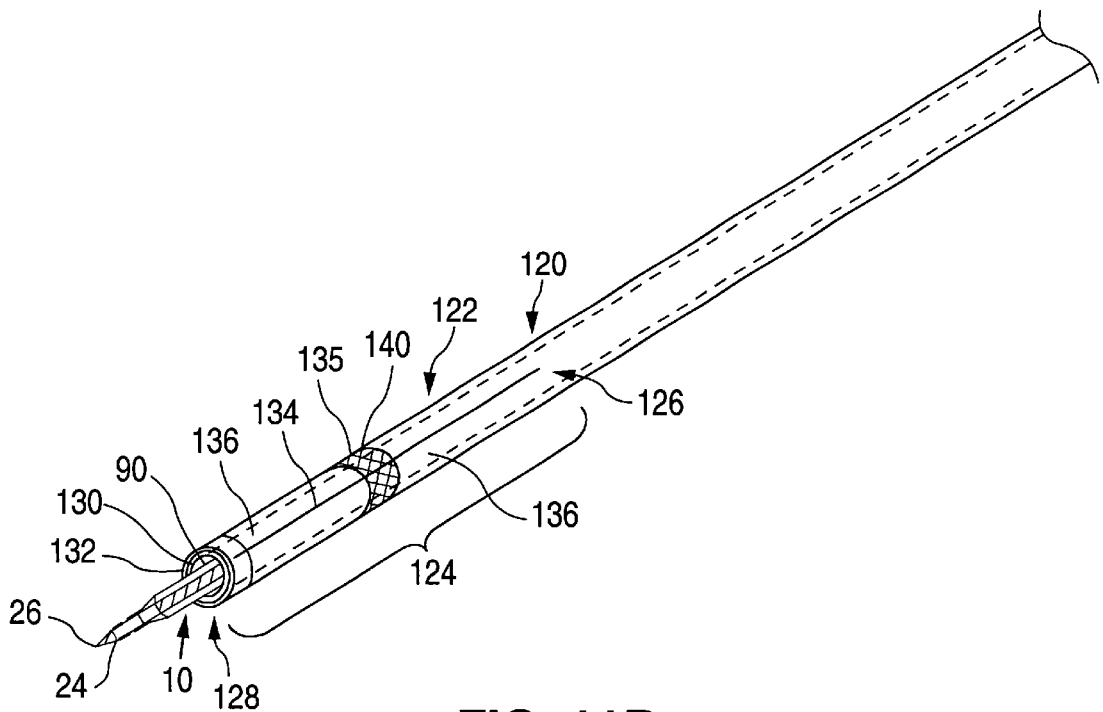
FIGS. 11B–11D are simplified illustrations of the catheter assembly in use with an embodiment of an anchoring device in accordance with the present invention.

FIGS. 11A and 11B are simplified illustrations of an embodiment of a guiding catheter 120 including an anchoring device 122 in accordance with the present invention.

In one embodiment, guiding catheter 120 can be a hollow sheath having an inner lumen that extends the length of the sheath. The inner lumen is sized to slidably receive various intraventricular devices, such as catheter assembly 10. Guiding catheter 120 can be made from any suitable superelastic material, such as polymers and copolymers of polyamides, polyolefins, polyurethanes, and the like.

In one embodiment, guiding catheter 120 includes anchoring device 122 disposed on a distal end of guiding catheter 120. As described in greater detail below, anchoring device 122 can be mounted to, or formed integrally with, guiding catheter 120. In this embodiment, anchoring device 122 includes an expandable portion 124, which has a proximal end 126 and a distal end 128. Expandable portion 124 can include any type of expandable mechanism that can be used to secure the intraventricular device in position to prevent needle 26 from sliding out of position, when needle 26 is being pushed into the target tissue. What follows is a description of various embodiments of guiding catheter 120 including anchoring device 122.

In one embodiment, as shown in FIG. 11B, expandable portion 124 can include a first tube 130 disposed concentrically within a second tube 132. First tube 130 and second tube 132 are coupled together using a coupling device 133 or other means of mating the tubes at distal end 128 of guiding catheter 120. To allow expandable portion 124 to expand, second tube 132 can have a pattern of one or more slits 134, which extend axially about the circumference of second tube 132. Slits 134 can be any suitable length L. Length L can be determined by the application and intended use of anchoring device 122. The space defined between each slit 134 defines a strut 136.

Figure 11C:
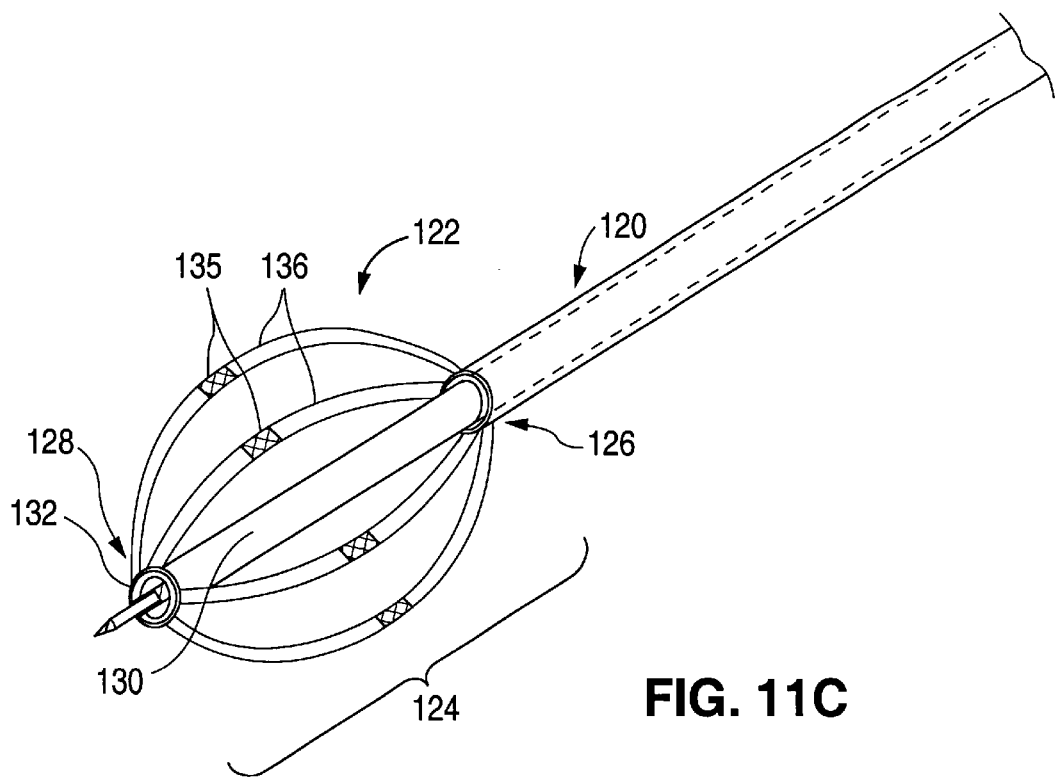

As shown in FIG. 11C, expandable portion 124 is designed to expand. Accordingly, anchoring device 122 can be forced from a first position or collapsed configuration of expandable portion 124 (FIG. 11B), to a second position or deployed configuration (FIG. 11C). Due to the superelastic nature of struts 136, in the deployed configuration, struts 136 can be forced outward to contact the tissue surface, for example, the walls of a vessel, the atria or atrium of the heart or a ventricle of the heart.

Figure 11E:
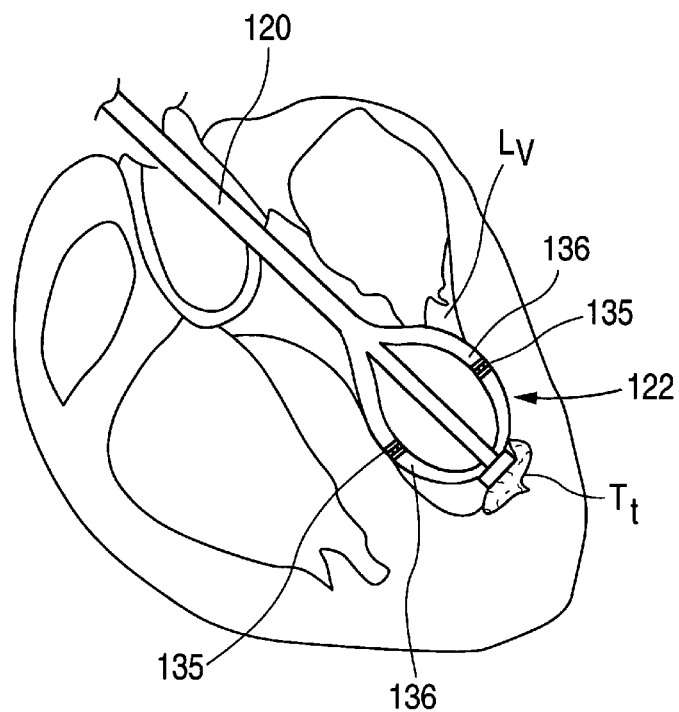
FIG. 11E is an exemplary illustration of an embodiment of the anchoring device of FIG. 11A deployed in the left ventricle of the human heart in accordance with the present invention.
Figure 11D:
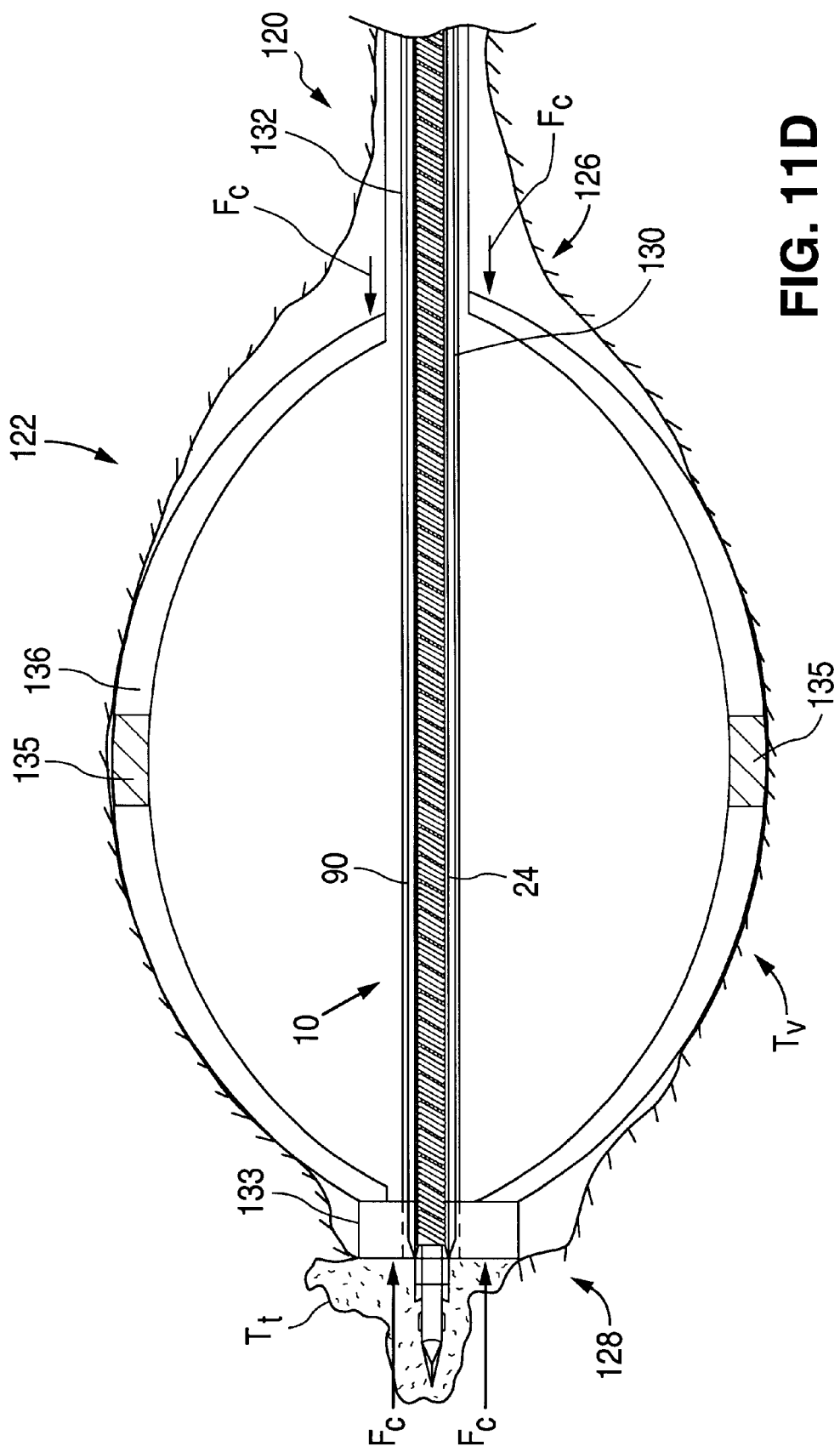

As understood with reference to FIG. 11D, distal end 128 of guiding catheter 120 can be fixed against target tissue $T_t$. In this embodiment, second tube 132 can be moved (e.g. pushed) relative to first tube 130 in an axial direction toward distal end 128. The result of the relative movement between first tube 130 and second tube 132 creates a compressive force $F_c$. As a result of the compressive force $F_c$, struts 136 of second tube 132 flex outward to contact the surrounding tissue $T_s$. Catheter assembly 10 can be moved through the inner lumen of guiding catheter 120 to be in position for deployment of needle 26 into target tissue $T_t$. First tube 130 is compressed against and, thus, holds catheter assembly 10 (i.e., outer member 90 and inner member 24) in position for deployment of needle 26. The friction as well as the compressive nature of the contact between struts 136 and the tissue surface $T_s$, and the compressive nature of the contact between first tube 130 and catheter assembly 10, prevents movement of catheter assembly 10, facilitating the advancement of needle 26 into the target tissue $T_t$.

FIG. 11E is an exemplary illustration of an embodiment of anchoring device 122 deployed in the left ventricle of the human heart. The flexible nature of struts 136 can act as a dampening device for catheter assembly 10. As a dampening device, anchoring device 122 reduces the influence of the beating human heart on the placement of needle 26, which lessens the possibility that needle 26 may be inadvertently removed from target tissue $T_t$.

FIG. 12A is a cut-away view of yet another embodiment of anchoring device 122 in use with a ventricular device, such as catheter assembly 10. In this embodiment, expandable portion 124 of anchoring device 122 can be a balloon 140. Balloon 140 can be formed from a balloon wall or membrane, which is selectively inflatable to dilate from a collapsed configuration (FIG. 12B) to a desired and controlled expanded configuration (FIG. 12C). Balloon 140 can be selectively inflated by supplying a fluid into an inflation lumen 150 at a predetermined rate of pressure. The fluid enters balloon 140 through port 152. The balloon wall is selectively deflatable, after inflation, to return to the collapsed configuration or a deflated profile.

Balloon 140 can be made from any suitable material, including, but not limited to, polymers and copolymers of polyolefins, polyamides, polyesters and the like. The specific material employed must be mutually compatible with the fluids employed in conjunction with balloon 140 and must be able to stand the pressures that are developed within balloon 140. The balloon wall can have any suitable thickness so long as the thickness does not compromise properties that are critical for achieving optimum performance. The properties include high burst strength, good flexibility, high resistance to fatigue, the ability to fold, the ability to cross and recross a desired region of treatment or an occluded region in a lumen, and low susceptibility to defect caused by handling. By way of example, and not limitation, the thickness can be in the range of about 10 microns to about 30 microns, the diameter of balloon 140 in the expanded configuration can be in the range of about 2 mm to about 10 mm or longer, and the length can be in the range of about 3 mm to about 40 mm or longer, the specific specifications depending on the procedure for which balloon 140 is to be used and the anatomy and size of the target area in which balloon 140 is to be inserted.

FIG. 12B is a simplified view of the left ventricle LV of the human heart with guiding catheter 120 with anchoring device 122, namely balloon 140 deployed therein. In FIG. 12A balloon 140 is in a deflated configuration to allow for easy insertion into the left ventricle LV. As shown in FIG. 12C, once in position, fluid received into balloon 140 through inflation lumen 150 and port 152 causes balloon 140 to inflate. The friction and compressive forces created between balloon 140 and the tissue surface prevents movement of catheter assembly 10, during the deployment of needle 26 into target tissue 105. To remove balloon 140, the fluid can be removed from a balloon 140 allowing balloon 140 to collapse.

FIG. 13 is an illustration of an alternative embodiment of expandable portion 124. In this embodiment, anchoring device 122 includes three inflatable sections, a distal section 142, a medial section 144, and a proximal section 146. Each section 142, 144, and 146 can be selectively inflated by supplying a fluid into inflation lumen 150 at a predetermined rate of pressure. The fluid enters each section through ports 152. The balloon wall is selectively deflatable, after inflation, to return to the collapsed configuration or a deflated profile. In one embodiment, distal section 142 and proximal section 146 can taper at any suitable angle θ, typically between about 15° to less than about 90°, when anchoring device 122 is in the expanded configuration to increase the holding capability of the sections. The friction and compressive forces created between each section 142, 144, and 146 and the tissue surface prevents movement of catheter assembly 10, during the deployment of needle 26 into the target tissue.

Referring now to FIGS. 11A–11D, 12A and 13, a radiopaque marker 135, or alternatively a plurality of radiopaque markers 135, can be disposed on a portion of expandable portion 124 to indicate to the operator the location of anchoring device 122. In general, radiopaque markers 135 may be made from a variety of suitable materials opaque to X-rays, such as platinum, gold, tungsten, tantalum and the like, to act, for example, as a marker to aid in positioning anchoring device 122. In one embodiment, illustrated for example in FIG. 11A, a lead wire (not shown) may be coupled to at least one radiopaque marker 135 to provide positioning feedback. The lead wire provides a path for electrical signals to be passed back and forth between markers 135 and a receiver (not shown). In one embodiment (FIG. 11E), the target treatment area, such as the left ventricle LV of the heart, can be mapped. The use of radiopaque markers for this purpose is well known and understood by those of ordinary skill in the art.

The therapeutic substances that may be delivered through needle 26 during a procedure can include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® an antiplatelet drug from Centocore). Examples of suitable antimitotic agents include methotrexate, azathioprine, vincristine, vinblastine, fluorouracil, adriamycin, mutamycin and actinomycin D. Examples of suitable cytostatic or antiproliferative agents include angiopeptin (a somatostatin analogue from Ibsen), angiotensin converting enzyme inhibitors such as Captopril® (available from Squibb), Cilazapril® available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as Platelet-derived Growth Factor (PDGF) receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. An example of an antiallergic agent includes Permirolast potassium. Other therapeutic substances or agents which may be appropriate include alpha-interferon, genetically engineered epithelial cells, dexamethasone, and growth factors such as FGF, PDGF, and VEGF. While the foregoing therapeutic substances or agents are well known for their preventative and treatment properties, the substances or agents are provided by way of example and are not meant to be limiting. Other therapeutic substances which are currently available or that may be developed are equally applicable for use with the present invention. The treatment of patients using the above-mentioned medicines is well known to those of ordinary skill in the art.

While particular embodiments of the present invention have been shown and described, it will be obvious to those having ordinary skill in the art that changes and modifications can be made without departing from this invention in its broader aspects. Therefore, the appended claims are to encompass within their scope all such changes and modifications as fall within the scope of the invention.

What is claimed is:

1. A medical implement comprising:
   an outer member having a proximal end, a distal end, and a lumen extending therethrough;
   an inner member having a proximal portion, a distal portion and a needle coupled to said distal portion, said inner member being slidably disposed in said outer member lumen, and said inner member having a plurality of indentations for increasing the flexibility of said distal portion of said inner member; and
   a steering assembly coupled to said inner member for steering said needle to a target location.

2. The medical implement of claim 1, wherein said outer member comprises a polymer sheath.

3. The medical implement of claim 1, further comprising an anchoring device for holding said needle in contact with said target location.

4. The medical implement of claim 1, wherein said inner member comprises a hypotube having a lumen extending therethrough.

5. The medical implement of claim 1, wherein said inner member comprises a coiled member including a first coil layer and a second coil layer, said first coil layer being more tightly wound than said second coil layer to increase the flexibility of said inner member.

6. The medical implement of claim 1, wherein said steering assembly comprises a first steering tendon, and a second steering tendon, wherein each of said first and second steering tendons can cause said distal portion of said inner member to flexibly bend.

7. The medical implement of claim 6, wherein said first steering tendon is coupled to a first puller and said second steering tendon is coupled a second puller, said pullers are configured to apply a tension to said steering tendons.

8. The medical implement of claim 1, wherein said inner member is capable of being moved relative to said outer member between a first position, where said needle is in a retracted position and a second position, where said needle is in an extended position.

9. The medical implement of claim 7, wherein said first and second pullers are ring-shaped and rotatably disposed around said proximal portion of said inner member such that rotation of each puller in a first direction around said proximal portion of said inner member increases the tension applied to the respective steering tendon and rotation in a second direction around said proximal portion of said inner member opposite the first direction decreases the tension applied to the respective steering tendon.

10. The medical implement of claim 9, wherein said first and second pullers have an annular groove therearound, and wherein each of said steering tendons has a portion disposed in said annular groove of said associated puller.

11. A medical implement comprising:
  a translating body assembly having a substantially flexible distal portion;
  a fixed body assembly configured to be mated with said translating body assembly, said translating body assembly being moveable relative to said fixed body assembly;
  a first steering tendon coupled to said distal portion of said translating body assembly to move said distal portion in a first direction; and
  a second steering tendon coupled to said distal portion of said translating body assembly to move said distal portion in a second direction, wherein said first steering tendon is operably engaged with a first puller assembly via a first biasing element and said second steering tendon is operably engaged with a second puller assembly via a second biasing element.

12. The implement of claim 11, wherein said translating body assembly comprises an outer member and an inner member slidably disposed in said outer member, wherein said inner member includes modification to provide said substantially flexible distal portion.

13. The implement of claim 12, wherein said inner member comprises a hollow hypotube.

14. The implement of claim 11, wherein said translating body assembly comprises a needle extending out from said distal portion for delivering a therapeutic substance.

15. The implement of claim 11, wherein said relative movement between said translating body assembly and said fixed body assembly causes an injection port coupled at a distal end of said translating body assembly to move between a first position where said injection port is provided inboard of said translating body assembly and a second position where said injection port is outboard of said translating body assembly.

16. The implement of claim 15, further comprising an anchoring device for holding said injection port in contact with a target location within the human body.

17. A medical device, comprising:
  an elongated member for inserting in a body lumen;
  a steering tendon coupled at one end to a distal portion of said elongated member to flex said distal portion of said elongated member; and
  a pulling assembly coupled to the other end of said steering tendon for applying tension to said steering tendon, said steering tendon being coupled to said pulling assembly by a biasing element.

18. The device of claim 17, wherein the biasing element is a spring.

19. The device of claim 17, additionally comprising a needle in fluid communication with said elongated member for deliver of a therapeutic substance.

20. A medical implement for delivering a therapeutic substance to a target area within the human body comprising:
  a catheter body having a proximal end, a distal end, and a lumen extending there between; an intraventricular device moveable relative to said catheter body, said intraventricular device including a plurality of indentations for increasing the flexibility of a distal portion of said intraventricular device; a injection element in fluid communication with said intraventricular device for delivering a therapeutic substance; and an anchoring device positioned proximate to said distal end of said catheter body, said anchoring device configured to maintain said intraventricular device in a stationary position during delivery of said therapeutic substance.

21. The medical implement of claim 20, wherein said anchoring device comprises a plurality inflatable sections spaced apart along a longitudinal axis of said catheter body, each inflatable section capable of being inflated independent of the other inflatable sections.

22. The medical implement of claim 20, wherein said catheter body comprises an inner catheter lumen telescopically disposed in an outer catheter lumen, said inner and outer catheter lumens being coupled at a distal end of said inner and outer catheter lumens, and wherein said anchoring device is defined by a plurality of struts extending axially around the circumference of said outer catheter lumen such that the telescopic movement of the outer catheter lumen over said inner catheter lumen toward said distal end causes said struts to expand in an outwardly bowed configuration for compressing said struts against an inner wall of a bodily lumen.

23. The medical implement of claim 21, wherein at least one of said inflatable sections has a tapered outer end that tapers at an angle between about 15 degrees and less than about 90 degrees when said inflatable section is inflated to an expanded configuration.

24. The medical implement of claim 20, wherein said catheter body comprises:
  a first tube; and
  a second tube disposed within said first tube, said first tube including struts that define said anchoring device, said struts configured to expand in an outwardly direction in response to relative movement between said first tube and said second tube.

25. The medical implement of claim 20, wherein said anchoring device comprises a balloon intergraded with said catheter body.

26. A medical implement for delivering a therapeutic substance to a target area within the human body comprising:

an outer member having a proximal end, a distal end, and a lumen extending therethrough;

an inner member having a proximal portion and a distal portion, said distal portion of said inner member having a plurality of indentations for increasing the flexibility of said distal portion; and a needle in fluid communication with said inner member, said inner member slidably disposed in said outer member between a first position, where said needle is inboard of said outer member lumen, and a second position, where said needle is outboard of said outer member lumen; and a steering assembly coupled to said distal portion of said inner member for moving said needle between a first direction and a second direction.

27. A method for delivering a therapeutic substance to a target area within the human body comprising:

delivering a medical implement to a target location within the human vasculature, said medical implement having an outer member, an inner member disposed in said outer member and a needle in fluid communication with said inner member, said inner member having a distal portion adjacent to said needle, said distal portion of said inner member having a plurality of indentations for increasing the flexibility of said distal portion of said inner member;

moving said inner member relative to said outer member between a first position, where said needle is within said outer member and a second position, where said needle is outside of said outer member;

applying a first tension to a first tendon to cause said needle to move in a first direction and/or applying a second tension to a second tendon to cause said needle to move in a second direction; and causing said needle to penetrate into said target location; and delivering said therapeutic substance to said target location.

28. The method of claim 27, wherein said first tension is applied to said first tendon by rotating a first puller coupled to an end of said first tendon via a first biasing element and wherein said second tension is applied to said second tendon by rotating a second puller coupled to an end of said second tendon via a second biasing element.

29. A medical implement comprising:

an outer member having a proximal end, a distal end, and a lumen extending therethrough;

an inner member having a proximal portion, a distal portion and a needle coupled to said distal portion, said inner member being slidably disposed in said outer member lumen;

a steering assembly coupled to said inner member for steering said needle to a target location; and wherein said inner member comprises a pattern of indentations formed on said distal portion for increasing the flexibility of said inner member.

30. A medical implement comprising:

a translating body assembly having a substantially flexible distal portion;

a fixed body assembly configured to be mated with said translating body assembly, said translating body assembly, being moveable relative to said fixed body assembly;

a first steering tendon coupled to said distal portion of said translating body assembly to move said distal portion in a first direction;

a second steering tendon coupled to said distal portion of said translating body assembly to move said distal portion in a second direction;

wherein said translating body assembly comprises an inner member having modification to provide said substantially flexible distal portion;

wherein said inner member comprises a hollow hypotube; and wherein said modification of said hypotube comprises indentations formed into said hypotube along said substantially flexible distal portion.

31. A medical implement comprising:

a translating body assembly having a substantially flexible distal portion;

a fixed body assembly configured to be mated with said translating body assembly, said translating body assembly being moveable relative to said fixed body assembly;

a first steering tendon coupled to said distal portion of said translating body assembly to move said distal portion in a first direction;

a second steering tendon coupled to said distal portion of said translating body assembly to move said distal portion in a second direction;

wherein said translating body assembly comprises an inner member having modification to provide said substantially flexible distal portion;

wherein said inner member comprises a hollow hypotube; and wherein said modification of said; hypotube comprises indentations formed into said hypotube, wherein said indentations are variably spaced along said substantially flexible distal portion.

32. A medical device, comprising:

an elongated member for inserting in a body lumen, said elongated member comprising a segment having grooves for increasing the flexibility of said segment of said elongated member;

a steering tendon coupled at one end to said elongated member for flexing said segment of said elongated member; and a pulling assembly coupled to the other end of said steering tendon for applying tension to said steering tendon.

33. The device of claim 32, additionally comprising a needle in fluid communication with said elongated member for deliver of a therapeutic substance.

* * * * *

UNITED STATES PATENT AND TRADEMARK OFFICE
CERTIFICATE OF CORRECTION

PATENT NO. : 6,623,448 B2
DATED : September 23, 2003
INVENTOR(S) : Renee C. Slater It is certified that error appears in the above-identified patent and that said Letters Patent is hereby corrected as shown below:

Column 5,
Line 63, change "First steering tendon. 28" to -- First steering tendon 28 --.

Column 16,
Line 4, change "configured.to be" to -- configured to be --.
Line 6, change "assembly,being" to -- assembly being --.
Line 42, change "of said; hypotube" to -- of said hypotube --.

Signed and Sealed this

Twenty-fifth Day of November, 2003

JAMES E. ROGAN
*Director of the United States Patent and Trademark Office*